US008216158B2

(12) United States Patent
Johnson

(10) Patent No.: US 8,216,158 B2
(45) Date of Patent: Jul. 10, 2012

(54) IMPLANTATION OF A MEDICAL DEVICE WITHIN A LUMEN

(75) Inventor: Blake D. Johnson, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1743 days.

(21) Appl. No.: 11/186,414

(22) Filed: Jul. 20, 2005

(65) Prior Publication Data

US 2007/0021736 A1      Jan. 25, 2007

(51) Int. Cl.
*A61B 5/103* (2006.01)
(52) U.S. Cl. .................................................. 600/593
(58) Field of Classification Search .................. 600/593, 600/112, 377; 604/117, 164.01; 607/133; 606/119
See application file for complete search history.

(56) References Cited

U.S. PATENT DOCUMENTS

| 4,141,365 A * | 2/1979 | Fischell et al. ................ 600/377 |
| 5,080,663 A | 1/1992 | Mills et al. |
| 5,383,260 A | 1/1995 | Deschenes et al. |
| 5,507,754 A * | 4/1996 | Green et al. ................... 606/139 |
| 5,549,617 A | 8/1996 | Green et al. |
| 5,690,691 A | 11/1997 | Chen et al. |
| 5,755,371 A | 5/1998 | Huang |
| 5,915,614 A | 6/1999 | Davignon et al. |
| 5,938,024 A | 8/1999 | Deschenes et al. |
| 5,975,398 A | 11/1999 | Evans |
| 6,210,039 B1 | 4/2001 | Teramachi |
| 6,285,897 B1 * | 9/2001 | Kilcoyne et al. ............... 600/350 |
| 6,293,952 B1 * | 9/2001 | Brosens et al. ................ 606/119 |
| 6,689,056 B1 * | 2/2004 | Kilcoyne et al. ............... 600/300 |
| 6,754,536 B2 | 6/2004 | Swoyer et al. |
| 7,020,531 B1 * | 3/2006 | Colliou et al. ................. 607/133 |
| 7,509,174 B2 * | 3/2009 | Imran et al. ................... 607/133 |
| 2002/0052653 A1 | 5/2002 | Durgin |

(Continued)

FOREIGN PATENT DOCUMENTS

WO    WO 02/089655 A2    11/2002

(Continued)

OTHER PUBLICATIONS

Notification of Transmittal of the International Preliminary Report on Patentability for corresponding PCT Application Serial No. PCT/US2006/027865 dated Jul. 20, 2007 (10 pages).

(Continued)

*Primary Examiner* — Max Hindenburg
*Assistant Examiner* — Fangemonique Smith
(74) *Attorney, Agent, or Firm* — Shumaker & Sieffert, P.A.

(57) ABSTRACT

A medical device implanted within a lumen of a patient, such as the esophagus, stomach, or another portion of the gastrointestinal tract, includes a device housing and a lead that extends from the device housing. An anchor member is located at a distal portion of the lead, and the lead includes one or more electrodes located between the device housing and the anchor member. A delivery system for implanting the medical device within the lumen includes an elongated delivery device and a needle. The needle includes a bore to receive the anchor member of the medical device. The delivery system inserts the anchor member through a passageway from the lumen, through the tissue, and back into the lumen.

25 Claims, 11 Drawing Sheets

U.S. PATENT DOCUMENTS

| | | | |
|---|---|---|---|
| 2002/0103424 | A1 | 8/2002 | Swoyer et al. |
| 2003/0167025 | A1 | 9/2003 | Imran et al. |
| 2004/0133089 | A1 | 7/2004 | Kilcoyne et al. |
| 2004/0143221 | A1 | 7/2004 | Shadduck |
| 2004/0243211 | A1 | 12/2004 | Colliou et al. |
| 2005/0209653 | A1 | 9/2005 | Herbert et al. |

FOREIGN PATENT DOCUMENTS

| | | | |
|---|---|---|---|
| WO | 2004021873 | A2 | 3/2004 |

OTHER PUBLICATIONS

European Examination Report dated Jun. 25, 2010 for corresponding EP Application No. 06787722.5 (4 pgs.).

International Search Report and Written Opinion from corresponding PCT Application Serial No. PCT/US2006/027865 mailed Dec. 1, 2006 (15 pages).

\* cited by examiner

IMPLANTATION OF A MEDICAL DEVICE WITHIN A LUMEN

FIELD OF THE INVENTION

The invention relates to medical devices and, more particularly, to medical devices implanted within a lumen of a patient.

BACKGROUND

The gastrointestinal (GI) tract, which is an example of a lumen within patients, includes the esophagus, stomach, small intestine, large intestine and colon. Implantable medical devices (IMDs) may be used to deliver therapies to the GI tract, and monitor physiological parameters within the GI tract. For example, an IMD may deliver electrical stimulation to the stomach to suppress symptoms associated with gastroparesis, such as nausea, or to induce such symptoms as a treatment for obesity.

In the past, stimulation and sensing within the GI tract have been achieved by surgically implanting an IMD in the abdominal or thoracic cavity, and coupling the IMD to a lead that includes one or more electrodes or sensors. The lead may be attached to the wall of the GI tract, or advanced though the wall and into the GI tract. However, implantation of an IMD in this manner subjects the patient to the risks attendant to a surgical procedure.

Consequently, non-surgical techniques for implanting an IMD within the GI tract have been proposed. In general, the proposed techniques involve delivering an IMD to an implantation site within the gastrointestinal tract via an endoscope or other tubular delivery instrument. Typically, the IMD is secured to the GI tract wall so that it is not immediately passed through the GI tract and excreted by the patient.

For example, U.S. Pat. No. 6,689,056 to Kilcoyne et al. describes techniques for implanting a probe that includes a sensor in the GI tract via an endoscope. The probe includes a cavity and a pin that for attaching the probe to the wall of the GI tract. Similarly, U.S. Patent Application Publication No. 2004/0243211 by Colliou et al. describes an endoscopic delivery system, and an IMD that includes a cavity and pin for attaching the IMD to the wall of the GI tract.

As another example, U.S. Pat. No. 6,754,536 to Swoyer et al. describes a GI tract IMD comprising a housing enclosing circuitry and an elongated flexible member extending from the housing to an active fixation mechanism adapted to be fixed into the GI tract wall. A distal end of an esophageal catheter lumen is inserted through the esophagus into a GI tract cavity at a site of implantation. The IMD is fitted into the catheter lumen with the fixation mechanism aimed toward an opening at the distal end of the catheter, and the fixation mechanism is fixed to the GI tract wall via the opening. When the IMD exits the opening, the elongated flexible member bends into a preformed shape to bring the housing into contact with the GI tract wall. The fixation mechanism and the housing include electrodes.

Further, U.S. Patent Application Publication No. 2003/0167025 by Imran et al. describes an endoscopic delivery system for implanting an IMD comprising an electronics unit and an attachment device within the stomach. The attachment device may be integral with, or removably attachable to the electronics unit, and may include electrodes. The attachment device penetrates and extends through the stomach wall to anchor the electronics unit to the stomach wall. The electronics unit includes one or more features for receiving or otherwise coupling to the attachment device.

SUMMARY OF THE INVENTION

In general, the invention is directed to implantation of medical devices within a lumen of a patient, such as the esophagus, stomach or another portion of the gastrointestinal tract of the patient. More particularly, the invention is directed to medical devices for implantation within a lumen of the patient, and delivery systems and methods for implanting such medical devices within the lumen. A medical device according to the invention includes a tether member, and is attached to the luminal wall by the tether member. A device housing located at a proximal end of the tether member, and an anchor member located at a distal portion of the tether member keep the member within tissue of the luminal wall, attaching the medical device to the luminal wall. In some embodiments, the tether member comprises a lead that includes electrodes between the device housing and the anchor member. The electrodes may be located within the tissue of the luminal wall when the medical device is attached to the luminal wall.

Various embodiments of the present invention may provide solutions to one or more problems existing in the prior art with respect to prior techniques for implanting medical devices within a lumen. Such problems include, by way of example, the need for the device housings of prior medical devices to include fixation mechanisms to attach the medical devices to a luminal wall. The housings including such mechanisms may be relatively difficult and expensive to manufacture. Further, such fixation mechanisms may increase the size of the device housing. For example, some device housing fixation mechanisms require a chamber to be formed in the housing, which consumes a portion of the volume defined by the device housing that could otherwise contain electrical circuitry or other components of the medical device.

Additionally, in order to ensure that electrodes of prior medical devices maintained contact with tissue of a luminal wall, some prior medical devices have included electrodes in a device housing that includes a fixation structure to be fixed to the luminal wall, electrodes carried by a lead and formed in the shape of a fixation structure, such as tined or corkscrew electrodes, or a lead carrying multiple electrodes to be fixed to the luminal wall at multiple points, such as by sutures, staples, or the like. Including electrodes on a housing may cause the housing to be relatively difficult and expensive to manufacture, and electrodes in the form of a fixation structure may also be more expensive than other types of electrodes, such as ring electrodes. Further, implantation techniques involving such housings, electrodes, or multiple fixation steps may be relatively lengthy and difficult for a physician to perform.

Various embodiments of the present invention may be capable of solving at least some of the foregoing problems. For example, a medical device according to the invention is attached to a luminal wall by a tether member and, therefore, may not require a device housing that includes a fixation structure. Further, in embodiments in which the tether member comprises a lead, electrodes carried by the lead are located within the tissue of the luminal wall, without requiring the electrodes to be formed in the shape of a fixation structure or to be fixed to the luminal wall at multiple points.

Various embodiments of the invention may possess one or more features for solving at least some of the aforementioned problems in the existing art. For example, a medical device for implantation in a lumen of a patient according to the invention includes a device housing sized for introduction into the lumen, a tether member that includes a proximal end that is coupled to the device housing, and an anchor member located at a distal portion of the tether member. The tether member may be a lead includes at least one electrode located between the proximal end and the anchor member and coupled to the electrical circuitry within the device housing.

The medical device is attached to the luminal wall by the tether member. More particularly, a device housing located at a proximal end of the tether member, and an anchor member located at a distal portion of the tether member keep the tether member within tissue of the luminal wall, attaching the medical device to the luminal wall. In embodiments in which the tether member is a lead, electrodes between the device housing and the anchor member are located within the tissue of the luminal wall when the medical device is attached to the luminal wall.

A system for implantation of a medical device within a lumen of a patient may include an elongated delivery device, such as an endoscopic delivery device, with a distal portion that defines a cavity. The system may also include a vacuum port to draw tissue of a luminal wall into the cavity, a needle, and an ejection tool. The needle and ejection tool may be advanceable to the distal portion of the elongated delivery device, e.g., via an axial working channel through the delivery device, and manipulated by a user at a proximal end of the delivery device.

The needle defines a bore that receives the anchor member of the medical device. In some embodiments, the anchor member is elongate, and may be substantially cylindrical. With the needle advanced to a position within or proximate to the cavity of the elongate delivery device, a user of the delivery system may insert the anchor member into the bore of the needle, effectively coupling the medical device to the delivery device. The user may then introduce the medical device and the delivery device into a lumen of the patient, and advance the delivery device and the medical device to an implantation location.

The needle may further define a slot that extends from a distal end of the needle, and a connecting member that connects the elongate element to the tether member, or the tether member itself, may pass through the slot when the anchor member is received by a bore of the needle. The slot may extend axially from the distal end of the needle, and a width of the slot may be less than a width of the bore to facilitate retention of the elongate element within the bore.

The widths of the bore and the anchor member may substantially correspond. Additionally, the widths of the slot and the connecting member or tether member may substantially correspond. In some embodiments, the anchor member and the bore, or the connecting member or tether member and the slot, are sized such that they frictionally engage each other when the anchor member is inserted into the bore. Through such frictional engagement, the anchor member may be retained in the bore, and the medical device may thus remain coupled to the delivery device during the advancement of both to an implantation site. The width of the anchor member may be less than approximately 0.1 inches and, more preferably, may be within a range from approximately 0.04 inches to approximately 0.06 inches. In some embodiments, the width of anchor member may be approximately 0.05 inches.

The vacuum port draws tissue of the luminal wall at the implantation site into the cavity defined by the distal portion of the delivery device. With the anchor member received by the bore, a user may advance the needle into the cavity and through the tissue disposed in the cavity to form a passageway from the lumen, through the tissue, and back into the lumen. The user may then advance an ejection tool through the bore of the needle to eject the anchor member from the bore. Advancing the needle through the tissue places the tether member within the passageway, e.g., within the tissue of the luminal wall, to attach the medical device to the luminal wall. When the anchor member is ejected from the bore, the anchor member is placed on a first side of the passageway while the device housing of the medical device coupled to the lead is located on a second side of the passageway. The anchor member and the device housing keep the tether member within the passageway.

The details of one or more embodiments of the invention are set forth in the accompanying drawings and the description below. Other features, objects, and advantages of the invention will be apparent from the description and drawings, and from the claims.

DETAILED DESCRIPTION OF THE PREFERRED EMBODIMENTS

Figure 1:
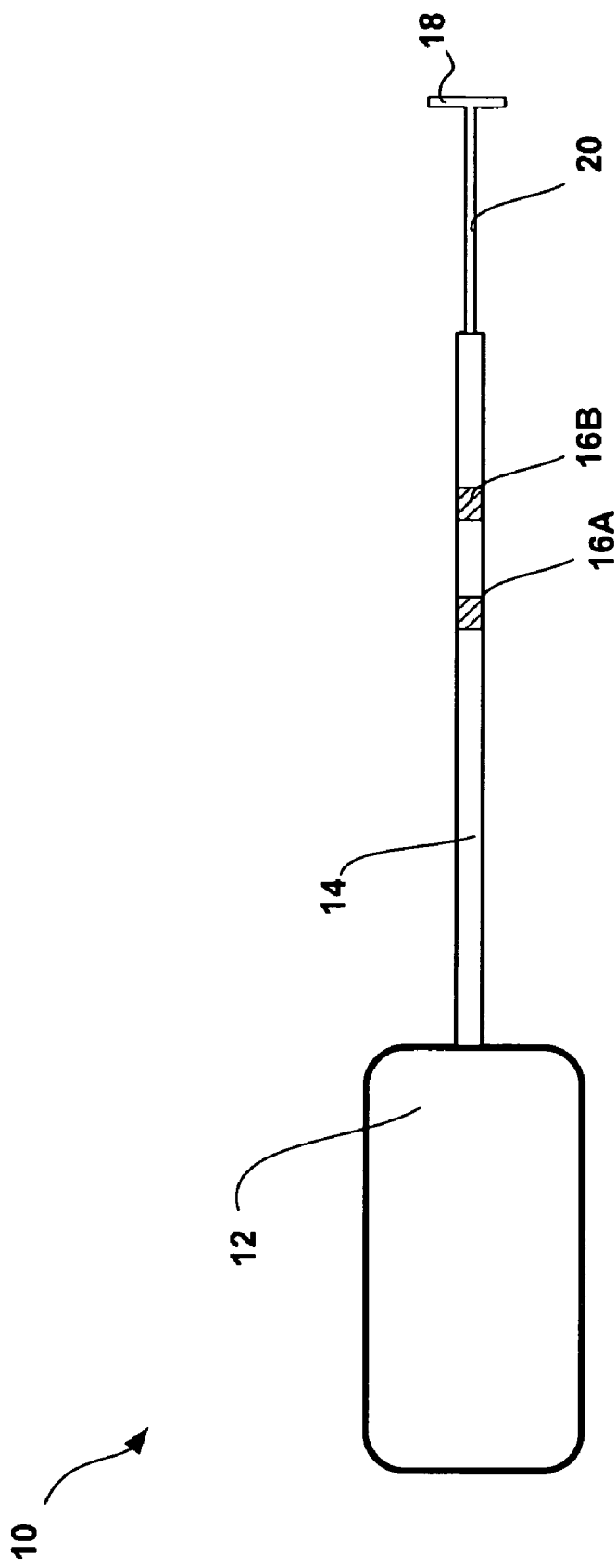
FIG. 1 is a side-view diagram illustrating an example medical device that may be implanted within a lumen of a patient according to the invention.

FIG. 1 is a side-view diagram illustrating an example medical device 10 that may be implanted within a lumen of a patient according to the invention. Medical device 10 includes a device housing 12, and a tether member, which in the illustrated example takes the form of a lead 14 coupled to the device housing. As will be described in greater detail below, medical device 10 is attached to a wall of the lumen by the lead when implanted. Because medical device 10 is attached to a luminal wall by lead 14, device housing 12 need not include a fixation structure for this purpose. In embodiments in which housing 12 does not include a fixation structure, the housing may be smaller and less difficult and expensive to manufacture than prior housings that include such fixation structures.

Device housing 12 contains electronic circuitry, which is mounted within the housing. In some embodiments, medical device 10 delivers electrical stimulation to the luminal wall. In such embodiments, the electronic circuitry may include circuitry that generates electrical pulses for delivery to the luminal wall via electrodes. Additionally or alternatively, medical device 10 may sense physiological parameters of a patient from the location at which it is implanted within the lumen. In such embodiments, the electronic circuitry may include circuitry for conditioning and processing a signal received from electrodes or other sensors, such as bonded piezoelectric crystals, temperature sensors, chemical sensors, or pressure sensors.

Device housing 12 may be hermetically sealed and formed of any of a variety of biocompatible materials, such as stainless steel, titanium, polyethylene, or PTFE. In some embodiments, device housing 12 may include or be coated with silicone. For example, device housing 12 may be coated with a silicone gel. Further, as illustrated by FIG. 1, device housing 12 may have a substantially capsule-like shape, e.g., a substantially cylindrical shape with rounded, atraumatic edges. Housing 12 having a substantially capsule-like shape or silicone coating may ease introduction of medical device 10 into a body lumen, and reduce the likelihood of trauma to the tissue of the luminal wall resulting from such introduction. Although illustrated in FIG. 1 as having a substantially capsule-like shape, device housing may have any shape. Device housing 12 is sized for introduction into the lumen of a patient in which medical device 10 is to be implanted.

Because medical device 10 is attached to a luminal wall by lead 14, and device housing 12 may not need to include a fixation mechanism for this purpose, device housing 12 may have a substantially smooth and atraumatic surface. Further, fixation of medical device 10 may not require that device housing 12 include chambers, passageways, or the like to receive tissue of the luminal wall for fixation thereto. Consequently, substantially all of the volume defined by device housing 12 may be reserved for electronic circuitry, and the volume defined by device housing 12 may be smaller than the volume defined by device housings that include chambers, passageways, or the like. Because device housing 12 may not require a fixation mechanism, the device housing may be easier and less expensive to manufacture than device housings that include such fixation mechanisms. For example, device housing 12 with a substantially smooth, capsule-like shape may be easier to cast or mold than a device housing that includes a chamber, passageway, or the like for fixation.

Lead 14 may include a flexible elongated lead body, which may be formed of silicone or the like. In the illustrated embodiment, lead 14 carries electrodes 16A and 16B (collectively "electrodes 16"). Electrodes 16 may be ring electrodes, and may be formed of any of a variety of conductive and biocompatible materials, such as platinum or tantalum, as is known in the art. The number of electrodes 16 illustrated in FIG. 1, and their position on lead 14, are merely exemplary.

Electrodes 16 may be used by the electronic circuitry within device housing 12 to deliver electrical stimulation, or to sense electrical activity or other physiological parameters. Lead 14 may include conductors, such as coiled conductors, which are coupled to the electrodes. A proximal end of lead 14 is coupled to device housing 12, and the device housing may include a feedthrough to couple the conductors of the lead to the electronic circuitry.

As shown in FIG. 1, medical device 10 also includes an anchor member 18 located at a distal portion of lead 14. In the illustrated example, anchor member 18 is located at the distal end of lead 14. In some embodiments, electrodes 16 are located between anchor member 18 and the proximal end of lead 14. In such embodiments, electrodes 16 will be located within the tissue of a luminal wall when medical device 10 is implanted in a lumen, allowing medical device 10 to deliver stimulation to or sense electrical activity within the luminal wall. Implantation of medical device 10 will be described in greater detail below.

Further, as shown in FIG. 1, anchor member 18 may be coupled to the distal end of lead 14 by a connecting member 20. In the illustrated example, anchor member 18 and connecting member 20 are elongate, which may facilitate coupling of the anchor member to a delivery device for implantation within a lumen. Further, at least the connecting member may be flexible to allow device housing 12 to move freely, e.g., rotationally about anchor member 18, when the anchor member is coupled to a delivery device for implantation. Anchor member 18 and connecting member 20 may be a unitary structure, and may be formed from any of a variety of biocompatible materials, such as polyethylene, polyvinylchloride, or silicone. In some embodiments, medical device 10 does not include connecting member 20, and anchor member 18 is coupled directly to, or formed at the distal portion of lead 14.

Figure 2A:
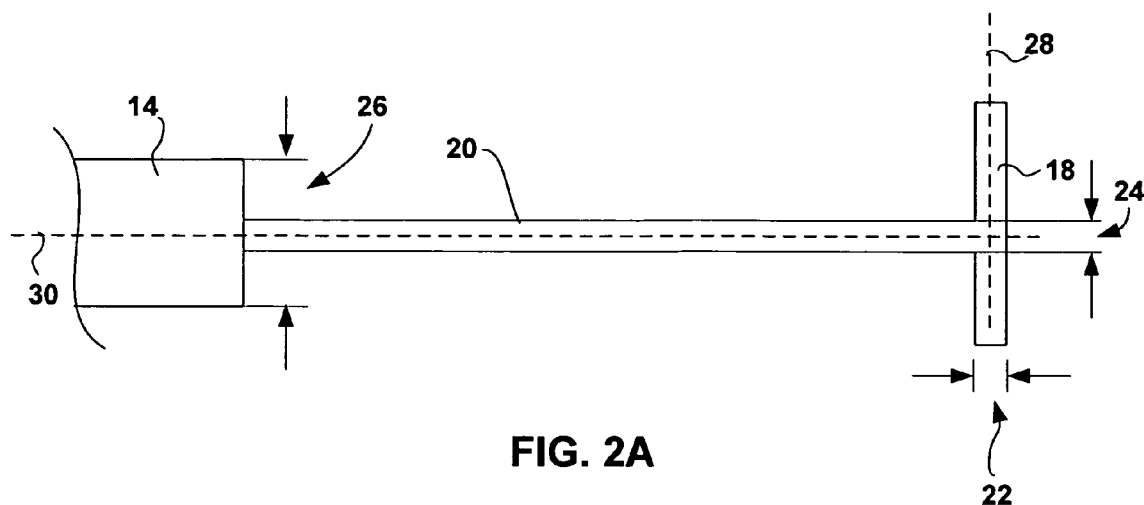
FIGS. 2A and 2B are side and top-view diagrams, respectively, illustrating an example anchor member of a medical device that may be implanted within a lumen of a patient according to the invention.
Figure 2B:
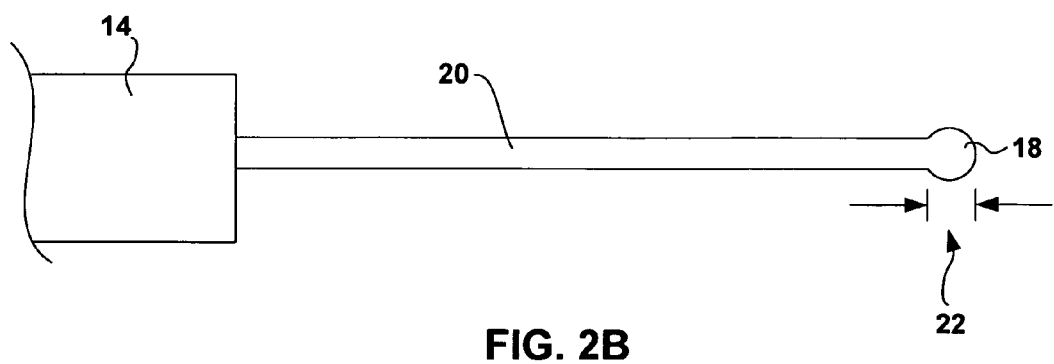

FIGS. 2A and 2B are side and top-view diagrams, respectively, further illustrating anchor member 18 and connecting member 20 connected to the distal end of lead 14. In the illustrated example, anchor member 18 has a substantially cylindrical shape, i.e., a circular cross-section, which may facilitate insertion into and ejection from a bore defined by a needle, as will be described in greater detail below. Connecting member 20 may also have a substantially cylindrical shape. However, the invention is not limited to medical devices 10 wherein anchor member 18 and connecting member 20 are elongate, or have substantially cylindrical shapes. For example, members 18, 20 may have spherical or cubical shapes, or may have cross-sections of any polygonal shape.

Anchor member 18 is sized to be received by a needle of a delivery device and, more particularly, a bore that is defined by the needle. As shown in FIGS. 2A and 2B, anchor member 18 has a width 22. In embodiments in which anchor member 18 is elongate, width 22 is a cross-sectional or transverse dimension of the anchor member. For example, where anchor member 18 has a circular cross-section, e.g., is substantially cylindrically shaped, the width 22 may be a diameter of the anchor member.

Width 22 may substantially correspond to the width or diameter of the bore defined by the needle. In some embodiments, width 22 may be less than approximately 0.1 inch. In some embodiments, width 22 may be within a range from approximately 0.04 inches to approximately 0.06 inches. In some embodiments, width 22 is approximately 0.05 inches. In such embodiments, width 22 may correspond to the width or diameter of the bores of ten to twenty gauge needles commonly delivered via endoscopes. In some embodiments, anchor member 18 may be sized to frictionally engage the needle when inserted into the bore thereof so that anchor member 18 may be retained in the bore during delivery of medical device 10 to an implantation site.

The needle may also have a slot formed through its wall, which may extend axially from the distal end of the needle. Connecting member 20 may be sized to be received by the slot, and may pass through the slot when anchor member 18 is received by the bore defined by the needle. Connecting member 20 may have a width 24, which may be a cross-sectional or transverse dimension of the connecting member when the connecting member is elongate, and may be a diameter of the connecting member when the connecting member has a substantially circular cross-section.

Width 24 of connecting member 20 may substantially correspond to a width of the slot formed in the needle. The width of the slot may be less than the width of the bore of the needle so that anchor member 18 is retained within the bore. Consequently, the width 24 of connecting member 20 may be less than width 22 of anchor member 18. Width 24 of connecting member 20 may be less than approximately 0.09 inches or may be within a range from approximately 0.03 inches to approximately 0.06 inches. Connecting member 20 may be sized to frictionally engage the slot formed in the needle so that connecting member 20 may be retained in the slot during delivery of medical device 10 to an implantation site.

In embodiments in which anchor member 18 is coupled directly to or formed at the distal portion of lead 14, the distal portion of the lead may pass through the slot formed in the needle. In such embodiments, a width 26 of the distal portion of lead 14 may be substantially as described above with reference to width 24 of connecting member 20. For example, in some embodiments, the width 26 of the distal portion of lead 14 may be within a range from approximately 0.02 to approximately 0.06 inches. In such embodiments, the distal portion of lead 14 may be sized to frictionally engage the slot.

As shown in FIG. 2A, a longitudinal axis 28 of anchor member 18 may be oriented substantially perpendicular to a longitudinal axis 30 of lead 14. In this manner, connecting member 20, or the distal portion of lead 14, may pass through the slot formed in the wall of the needle when anchor member 18 is received by the bore of the needle. This orientation of anchor member 18 may allow medical device 10 to travel along side of or behind a distal portion of a delivery device when advanced to an implantation site within a lumen of a patient.

Figure 3:
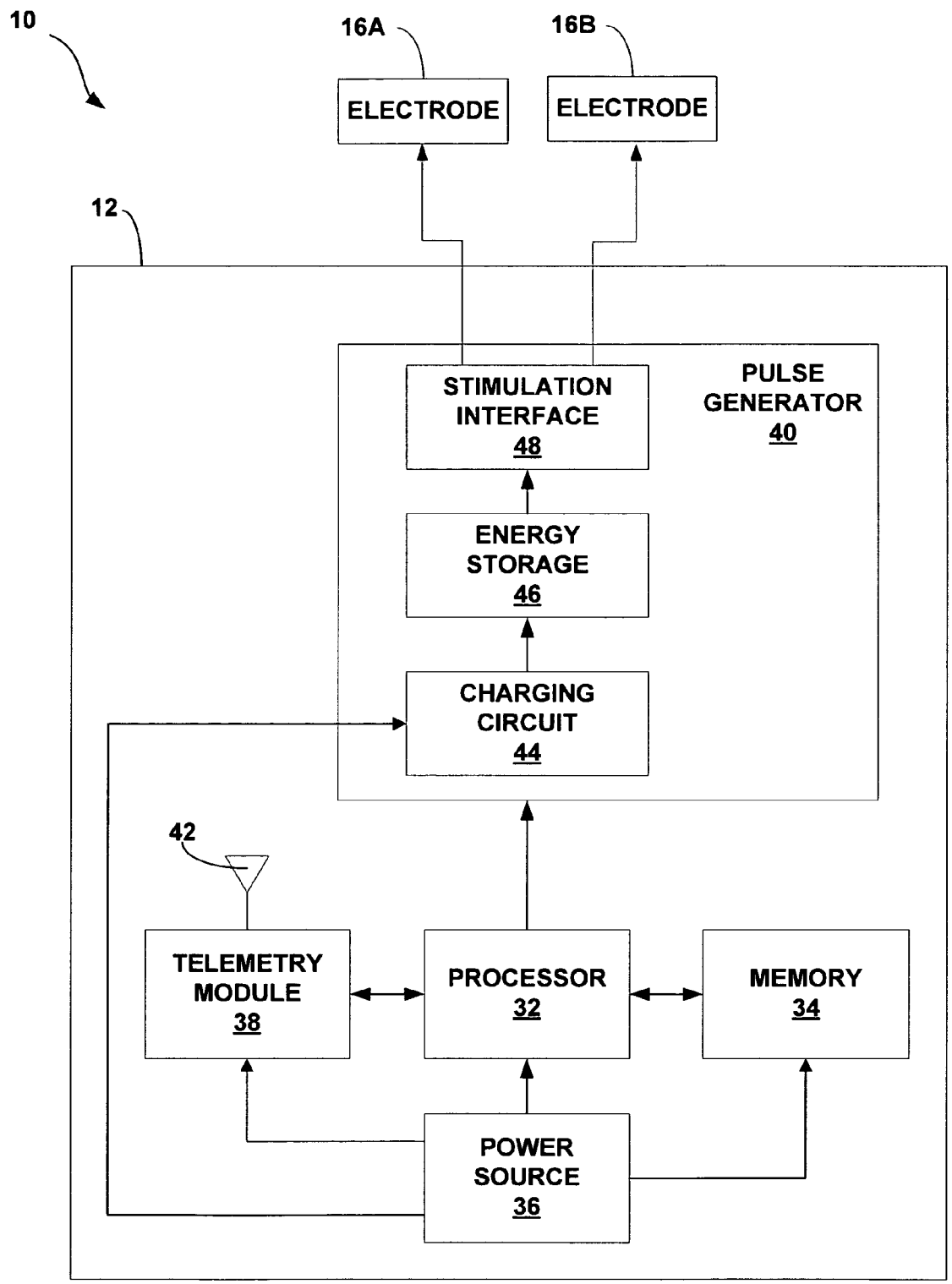
FIG. 3 is a block diagram further illustrating the medical device of FIG. 1.

FIG. 3 is a block diagram further illustrating medical device 10. More particularly, FIG. 3 illustrates electronic circuitry that may be housed within device housing 12 of medical device 10 according to an example embodiment in which medical device 10 delivers stimulation to tissue of a luminal wall when implanted within a lumen of patient. As indicated above, medical device 10 may additionally or alternatively sense physiological parameters of a patient from an implantation site within a lumen of the patient.

In the example of FIG. 3, medical device 10 may include a processor 32, memory 34, power source 36, telemetry module 38, pulse generator 40 coupled to electrodes 16A, 16B. Telemetry module 38 is optional and permits communication with an external controller or programmer for transfer of data and adjustment of stimulation parameters. Alternatively, in some embodiments, medical device 10 may exclude telemetry module 38, in which case all stimulation parameters may be preset and fixed within the medical device. Exclusion of telemetry module 38 may be desirable in some applications to achieve reductions in the size of medical device 10.

Processor 32 controls operation of medical device 10 and may include one or more microprocessors, digital signal processors (DSPs), application-specific integrated circuits (ASICs), field-programmable gate arrays (FPGAs), or other digital logic circuitry. Memory 34 may include any magnetic, electronic, or optical media, such as random access memory (RAM), read-only memory (ROM), electronically-erasable programmable ROM (EEPROM), flash memory, or the like. Memory 34 may store program instructions that, when executed by processor 32, cause the processor to perform the functions ascribed to it herein. For example, memory 34 may store instructions for processor 32 to execute in support of control of telemetry module 38 and pulse generator 40.

Telemetry module 38 may include a transmitter and receiver to permit bi-directional communication between medical device 10 and an external controller or programmer. In this manner, the external controller may transmit commands to medical device 10 and receive status and operational information from the medical device. Telemetry module 38 includes an antenna 42, which may take a variety of forms. For example, antenna 42 may be formed by a conductive coil or wire embedded in device housing 12. Alternatively, antenna 42 may be mounted on a circuit board within housing 12 carrying other components of medical device 10, or take the form of a circuit trace on the circuit board. If medical device 10 does not include a telemetry module 38, a magnetic reed switch may be provided in a circuit between power source 36 and the other components of the device so that, with the aid of an external magnet, the device may be turned on at the time the device is placed in the patient.

Power source 36 may take the form of a battery and power circuitry. In some embodiments, medical device 10 typically will be used temporarily, and therefore may not require substantial battery resources. Accordingly, the battery within power source 10 may be very small. An example of a suitable battery is a model 317 silver oxide battery often used to power watches. The model 317 battery has voltage of 1.55 volts and a capacity of 12.5 mA-hours and has a disk-like shape with a diameter of approximately 5.7 mm and a thickness of approximately 1.65 mm. With a typical range of power requirements of the stimulation waveform and the components of medical device 10, the model 317 battery can be expected to power the device for between approximately two weeks and eighteen months, depending on actual usage conditions.

Different types of batteries or different battery sizes may be used, depending on the requirements of a given application. In further embodiments, power source 36 may be rechargeable via induction or ultrasonic energy transmission, and includes an appropriate circuit for recovering transcutaneously received energy. For example, power source 36 may include a secondary coil and a rectifier circuit for inductive energy transfer. In still other embodiments, power source 36 may not include any storage element, and medical device 10 may be fully powered via transcutaneous inductive energy transfer.

Pulse generator 40 produces an electrical stimulation waveform with parameters selected to, for example, improve gastric motility, suppress nausea and vomiting, or induce a sensation of nausea or satiety. As shown in FIG. 2, pulse generator 40 includes a charging circuit 44, an energy storage device 46, and a stimulation interface 48. Charging circuit 44 accesses energy supplied by power source 36 to charge energy storage device 46, which may be one or more capacitors. Stimulation interface 48 amplifies and conditions charge from energy storage device 46 to produce an electrical stimulation waveform for application to electrodes 16A, 16B. As an example, pulse generator 40 may incorporate circuitry similar to the pulse generation circuitry in the ITREL 3 neurostimulator, commercially available from Medtronic, Inc. of Minneapolis, Minn.

Stimulation parameters, such as amplitude, frequency, pulse width, duty cycle and duration, may be selected to simply suppress symptoms, or actually treat the cause of the symptoms such as gastroparesis, post-operative ileus or some other disorder that disrupts stomach motility, or causes nausea and vomiting. In other embodiments, stimulation parameters may be selected to induce such symptoms to treat, for example, obesity. Stimulation parameters may also be selected for treatment of, for example, irritable bowel syndrome, functional dyspepsia, gastroesophageal reflux disease, or nausea and/or vomiting resulting from chemotherapy, treatment of post-operative ileus, or treatment of hyperemesis gravidarum.

In other words, processor 32 may be programmed, or pulse generator 40 may be otherwise configured, according to the stimulation requirements of any of a variety of particular disorders or conditions of a patient in which medical device 10 is implanted. Medical device 10 may be capable of extended or long-term use, or temporary use. In some embodiments, medical device 10 may be used for trial screening of gastroelectrical stimulation therapy, and the results of such trial stimulation may lead to long-term implantation of a more fully-featured, an potentially larger, medical device. In some embodiments, as will be described in greater detail below, how long medical device 10 is implanted within a patient, e.g., temporary or long-term, may be controlled by controlling the depth at which lead 14 (FIG. 1) is implanted within a luminal wall of the patient, or by selection of the materials of which anchor member 18 and/or connecting member 20 are formed.

In some embodiments, medical device 10 may additionally or alternatively be used to sense physiological parameters of a patient from an implantation location within a lumen of the patient. In such embodiments, the medical device may include signal conditioning circuitry, such as filters or amplifiers, to condition signals received from electrodes 16 or other sensors. Medical device 10 may also include an analog-to-digital converter to convert such signals to digital signals for processing by processor 32. Processor 32 may store the signals or physiological parameter values derived from the signals in memory 34, may provide such signals or parameter values to an external controller, programmer, or other processor via telemetry module 38, or may control delivery of stimulation by pulse generator 40 based on such signals or parameters. Medical device 10 may, for example, sense electrical or muscular activity, or pH, within the gastrointestinal tract, e.g., the stomach or esophagus. Medical device 10 may be capable of extended or temporary use for sensing.

Figure 4A:
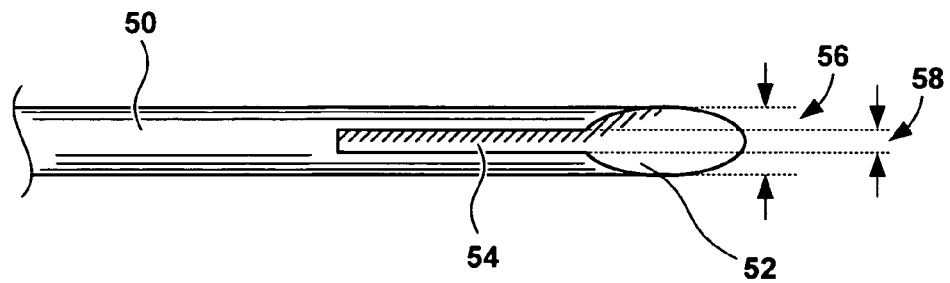
FIGS. 4A-4E are perspective diagrams illustrating components of a delivery system for implanting a medical device within a lumen of a patient according to the invention.

FIGS. 4A-4E are perspective diagrams illustrating components of a delivery system for implanting medical device 10 within a lumen of a patient according to the invention. As shown in FIG. 4A, delivery system includes a needle 50 that defines a bore 52 through the needle and includes a slot 54. Slot 54 may extend from the distal end of needle 50 in a substantially axial direction, as shown in FIG. 4A.

As discussed above, bore 52 receives anchor member 18 of medical device 10. A width 56, e.g., circumference, of bore 52 may substantially correspond with width 22 of anchor member. Width 56 may be less than approximately 0.11 inches, and within a range from approximately 0.05 inches to approximately 0.07 inches, which may correspond to ten to twenty gauge needles commonly delivered via endoscopes. In some embodiments, width 56 may be approximately 0.06 inches. Bore 52 may be sized such that needle frictionally engages anchor member 18 when the anchor member is inserted into the bore.

When bore 52 receives anchor member 18, connecting member 20 or a distal portion of lead 14 of the medical device may extend through slot 54. A width 58 of slot 54 may substantially correspond with width 24 of connecting member 20 or width 26 of a distal portion of lead 14. Width 58 may be less than width 56 of bore 52 to facilitate retention of anchor member 18 within the bore. Width 58 may be less than approximately 0.1 inches, or within a range from approximately 0.04 inches to approximately 0.07 inches. Slot 54 may be sized to frictionally engage connecting member 20 or lead 14 when bore receives anchor member, to retain connecting member 20 or lead 14 during advancement of medical device 10 to an implantation location.

Figure 4B:
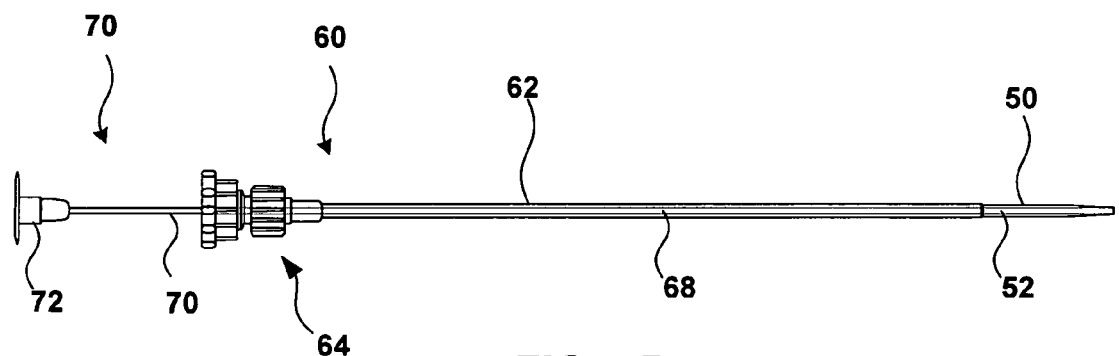

As illustrated in FIG. 4B, needle 50 is located at a distal end of a needle advancing tool 60. Needle advancing tool 60 includes an elongated element 62, needle 50 located at the distal end of elongated element 62, and a handle 64 located at a proximal end of elongated element 62. Needle 50 may be formed of, for example, stainless steel, titanium, polyvinylchloride, or any of a variety of other rigid, biocompatible materials. Elongated element 62 may be flexible to allow the elongated element to bend with a delivery device, which will be described in greater detail below, when the delivery device is advanced and steered to an implantation location within a body lumen. Elongated element 62 may be formed of, for example, polyethylene or silicone. Handle 64 may be formed of, for example, polyvinylchloride or polyethylene. Handle 64 and elongated element 62 define a lumen 68 that communicates with bore 52 of needle 50.

Figure 4C:
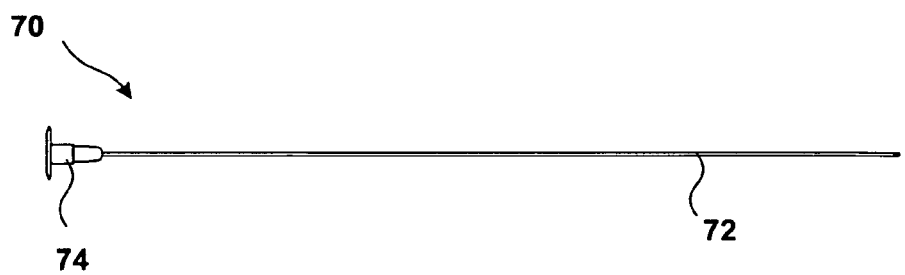

FIG. 4C illustrates an ejection tool 70, which includes an elongated element 72 and a handle 74. Elongated element 72 of ejection tool 70 may be sized to be received and advanced through lumen 68 and bore 52. Elongated element 72 may be rigid in an axial direction to facilitate advancement through lumen 68 and bore 52, and ejection of anchor member 18 from bore 52, but may be otherwise flexible to allow elongated element to 72 bend with elongated element 62. Elongated element 72 and handle 74 may be formed of, for example, polyvinylchloride or polyethylene.

Figure 4D:
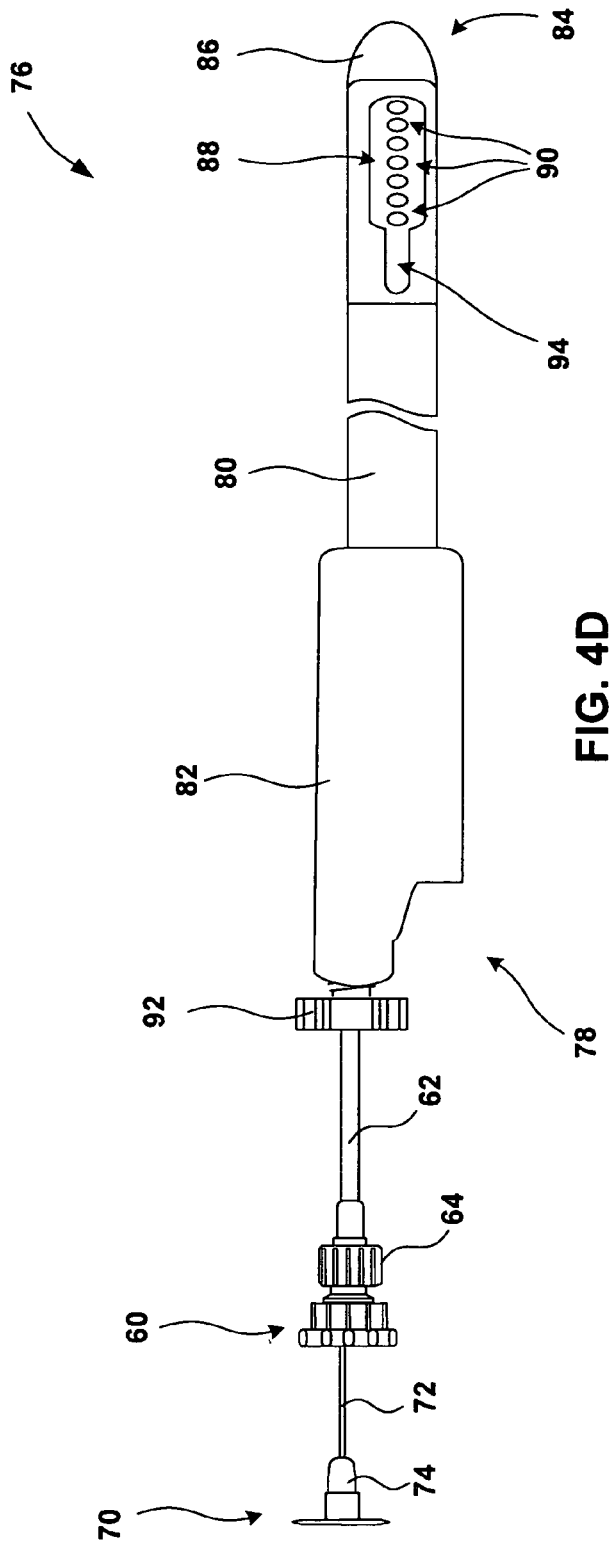

FIG. 4D illustrates a system 76 for implanting medical device 10 within a lumen of a patient. In addition to needle 50, needle advancing tool 60 and ejection tool 70, system 76 includes a delivery device 78. Delivery device 78 may be an endoscopic delivery device, and may include one or more lenses and electronics to allow a user to view images from the distal portion of delivery device 78.

Delivery device 78 comprises an elongate, flexible body portion 80. At a proximal end of body portion 80, delivery device 78 includes a handle 82. A user of delivery device 78 may use handle 82 to advance a distal portion 84 of body portion 80 to an implantation site within a lumen of a patient. In some embodiments, handle 82 may include one or more actuators coupled to wires or the like that extend through body portion and are fixed at distal portion 84. Through the actuators, the user may bend portion 80 and or distal portion 84 to steer the distal portion to the implantation site. A distal end 86 of delivery device 78 may be semispherical or otherwise rounded to ease introduction of delivery device 78 into a lumen of a patient, e.g., an esophagus. Delivery device 78 may be formed of any one or more of polyvinylchloride, polyethylene, or silicone.

Distal portion 84 of delivery device 78 defines a cavity 88 that is in fluid communication with a plurality of vacuum ports 90. Vacuum ports 90 may be in fluid communication with one or more lumen that extend through body portion 80 to handle 82. A user may apply vacuum pressure to vacuum ports 90 via the lumen within body portion 80 to draw tissue of a patient into cavity 88.

Handle 82 and body portion 80 may define a plurality of lumens that extend to distal portion 84. For example, such lumen may connect a lens or charge coupled device (CCD) located at distal portion 84 to handle 82, where images from the lens may be provided to a display, and an image from the lens or CCD may be viewed by a user of system 76. The lens or CCD may be located such that the user can view, for example, the interior of cavity 88 and/or an area ahead of the advancement of delivery device 78.

A lumen, e.g., a working channel, to receive needle advancing tool 60 may also extend from handle 82, through body portion 80, and communicate with cavity 88. A user of system 76 may advance needle advancing tool 60 through the lumen until needle 50 reaches cavity 88. A user may tighten a leur lock 92 located at handle 82, or the like, around needle advancing tool 60 by the user to prevent further advancement of needle 50 into cavity 88.

Figure 4E:
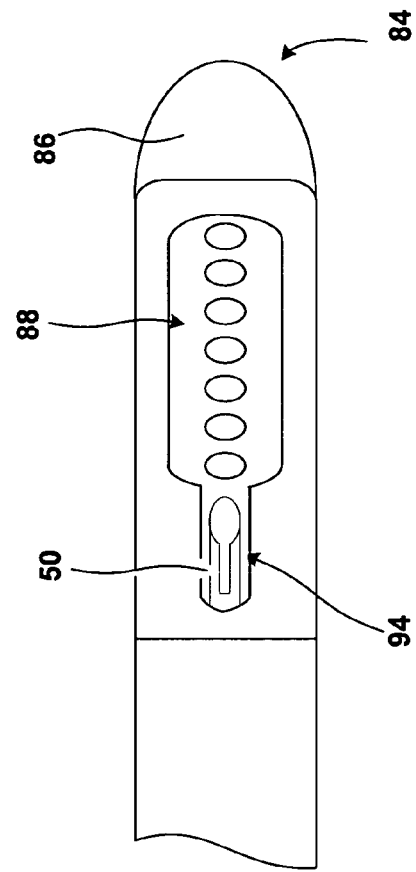

As illustrated in FIG. 4E, distal portion 82 of delivery device 78 may be formed with a slot 94 that extends from cavity 88 in a proximal direction. Slot 94 allows a user of system 76 to access needle 50 within a lumen or working channel of delivery device 78 prior to the needle being advanced into the cavity. With needle 50 positioned proximate to cavity 88, a user may insert anchor member 18 of medical device 10 (FIG. 1) into bore 52 (FIG. 4A) of needle 50 through slot 94. With anchor member 18 inserted in to bore 52 of needle 50, connecting member 20 or a distal portion of lead 14 of medical device 10 may extend through slot 54 of needle 50 and slot 94 of delivery device 78. In other embodiments, delivery device 78 may not include slot 94, and the user may partially advance needle 50 into cavity 88 to insert anchor member 18 into bore 52.

By inserting anchor member 18 into bore 52, a user of system 76 may effectively couple medical device 10 to delivery device 78. The user may then advance both distal portion 84 of delivery device 78 and medical device 10 to an implantation location, as will be described in greater detail below with reference to FIG. 5. The user may insert elongate element 72 of ejection tool 70 into lumen 68 (FIG. 4B) defined by needle advancing tool 60 prior to advancing delivery device 78 into the lumen of the patient, in which case a leur lock or the like at handle 64 of needle advancing tool 60 may be tightened to prevent the elongate element from prematurely ejecting anchor member 18 from bore. Alternatively, the user may insert elongate element 72 of ejection tool 70 into lumen 68 (FIG. 4B) defined by needle advancing tool 60 when the user wishes to eject the anchor member from the bore.

Figure 5:
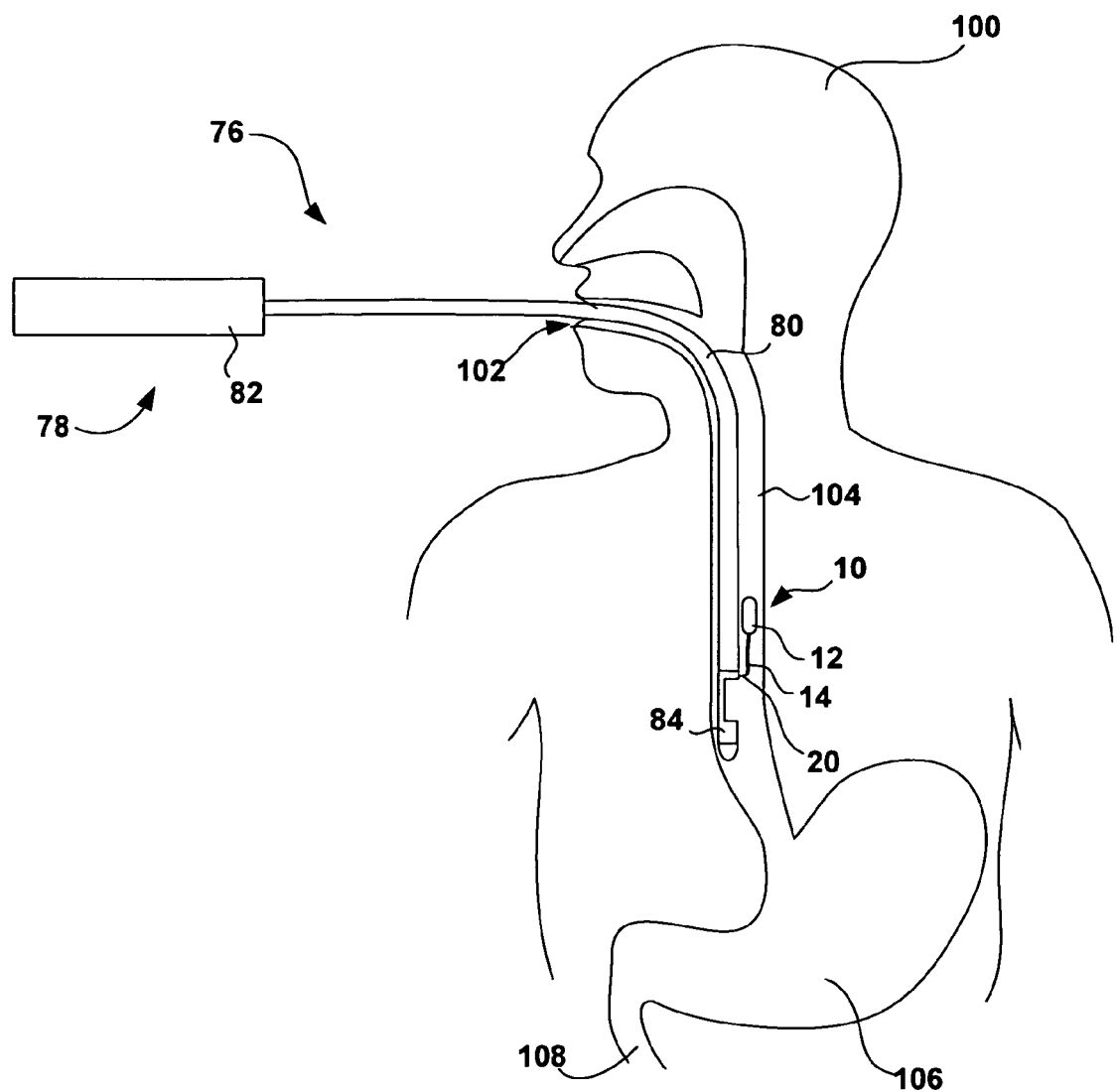
FIG. 5 is a conceptual diagram illustrating a medical device and delivery device of a delivery system in conjunction with a patient.

FIG. 5 is a conceptual diagram illustrating medical device 10 and delivery device 78 of delivery system 76 in conjunction with a patient 100. More particularly, FIG. 5 illustrates an example technique for implantation of medical device 10 within the gastrointestinal tract of patient 100. In the illustrated example, medical device 10 is connected to distal portion 84 of delivery device 78, e.g., anchor member 18 (FIG. 1) is received by bore 52 of needle 50 (FIG. 4A).

In the example illustrated by FIG. 5, a user manipulates handle 82 to advance distal portion 84 of delivery device 78 and medical device 10 an oral cavity 102 and into an esophagus 104 of patient 100. The user may advance distal portion 84 and medical device 10 to an implantation location, which may be within esophagus 104, a stomach 106 or a small intestine 108 of patient 100. However, the invention is not limited to implantation within the upper gastrointestinal tract, or within the gastrointestinal tract at all. Medical device 10 may be implanted within any lumen of patient 100.

As discussed above, a width 22 of anchor member 18 may substantially correspond to a width 56 of bore 52 of needle 50. Further, anchor member 18 may be sized to frictionally engage needle 50 when inserted into bore 52. The relative widths of anchor member 18 and bore 52, and frictional engagement between the anchor member and the needle may retain anchor member 18 within bore 52 during advancement of delivery device 78 and medical device 10 to an implantation location.

Additionally or alternatively, a width 24 of connecting member 20 or a width 26 of a distal portion of lead 14 may substantially correspond to a width 58 of slot 54 of needle 50. Further, the connecting member or lead may be sized to frictionally engage needle 50 when they pass through slot 54. The relative widths of the connecting member or lead and the bore, and frictional engagement e connecting member or lead and the needle may retain connecting member 20 within slot 54 during advancement of delivery device 78 and medical device 10 to an implantation location.

Frictional engagement between medical device 10 and needle 50 as described above may keep medical device 10 attached to delivery device 78 during advancement to an implantation location. In the illustrated example, device housing 12 is advanced to the implantation location alongside delivery device 78. In embodiments in which connecting member 20 and/or lead 14 are flexible, device housing 12 may be "pulled" to the implantation location by needle 50 located at distal portion 84 of delivery device 78, as illustrated in FIG. 5. In such embodiments, device housing 12 may travel to the implantation site very near elongate body 80 of delivery device 78 to present as small a total cross-sectional area to esophagus 104 as possible during delivery.

In other embodiments, a lumen through handle 82 and elongate body 80 of delivery device may be sized to receive housing 12. In such embodiments, needle 50 and attached medical device 10 may be advanced through the delivery device to an implantation location.

FIGS. 6A-6D are cross-sectional diagrams illustrating implantation of medical device 10 within a lumen of patient 100, such as esophagus 104 or stomach 106 shown in FIG. 5. As described above, a user of delivery system 76 (FIGS. 4A-4E) may advance needle delivery tool 60 including an elongate element 62 and needle 50 located at the distal end of elongate element 62 to distal portion 84 of delivery device 78 through a lumen 110 defined by elongate body 80 of delivery device 78. With needle 50 located proximate to cavity 88 defined by distal portion 84 of delivery device 78, the user may insert anchor member 18 of medical device 10 into bore 52 (FIG. 4A) of needle 50. When anchor member 18 is received by bore 52, connecting member 20 may extend through a slot 54 (FIG. 4A) of needle 50. With medical device 10 attached to delivery device 78 in this manner, the user may advance distal portion 84 and medical device 10 to an implantation location within the lumen.

Figure 6A:
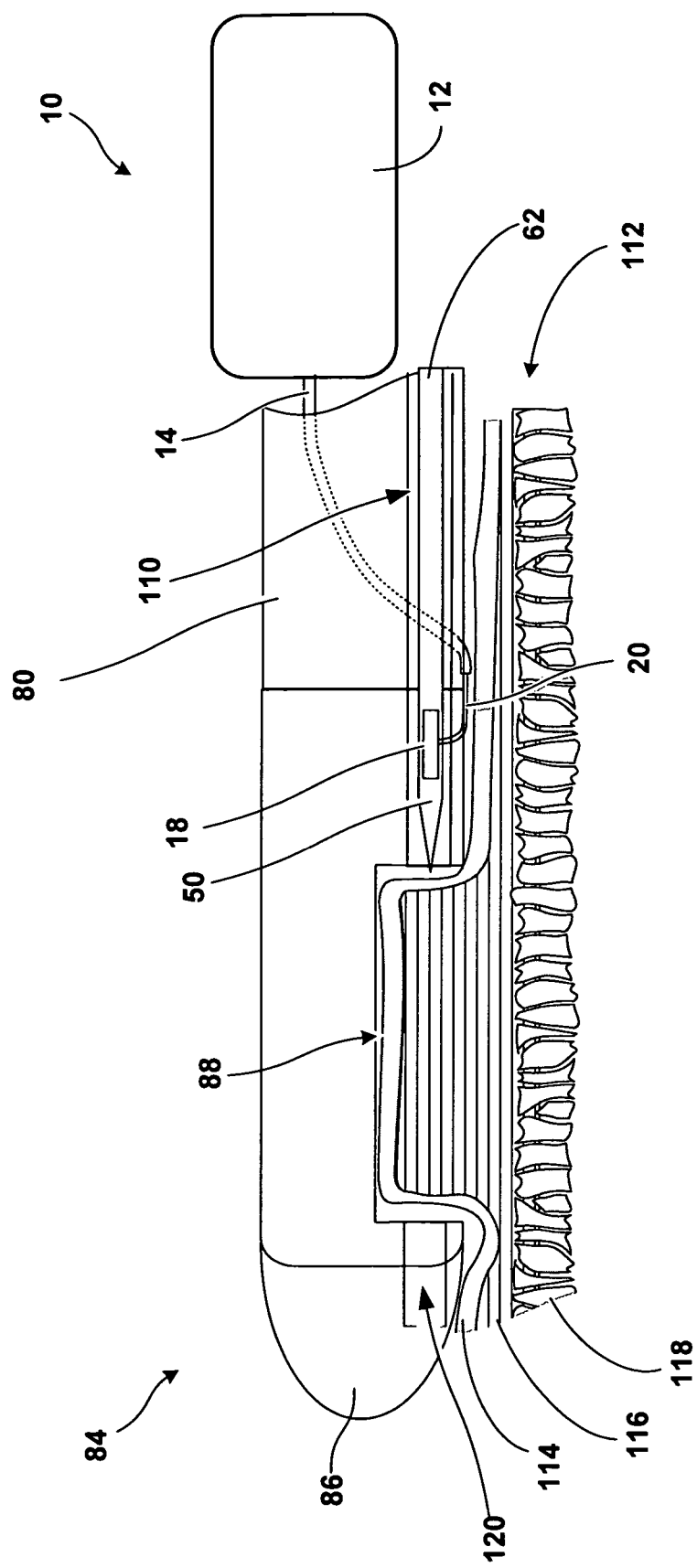
FIGS. 6A-6D are cross-sectional diagrams illustrating implantation of a medical device within a lumen of a patient according to the invention.

FIG. 6A illustrates distal portion 84 of delivery device 78 and medical device 10 proximate to a luminal wall 112 of patient 100 at the implantation location within the lumen. Luminal wall 112 includes a plurality of layers, such as a mucosal layer 114, submucosal layer 116 and muscular layer 118. As illustrated in FIG. 6A, the user may apply vacuum pressure to cavity 88 via vacuum ports 90 (FIGS. 4D and 4E) to draw tissue of luminal wall 112 into the cavity.

Figure 6B:
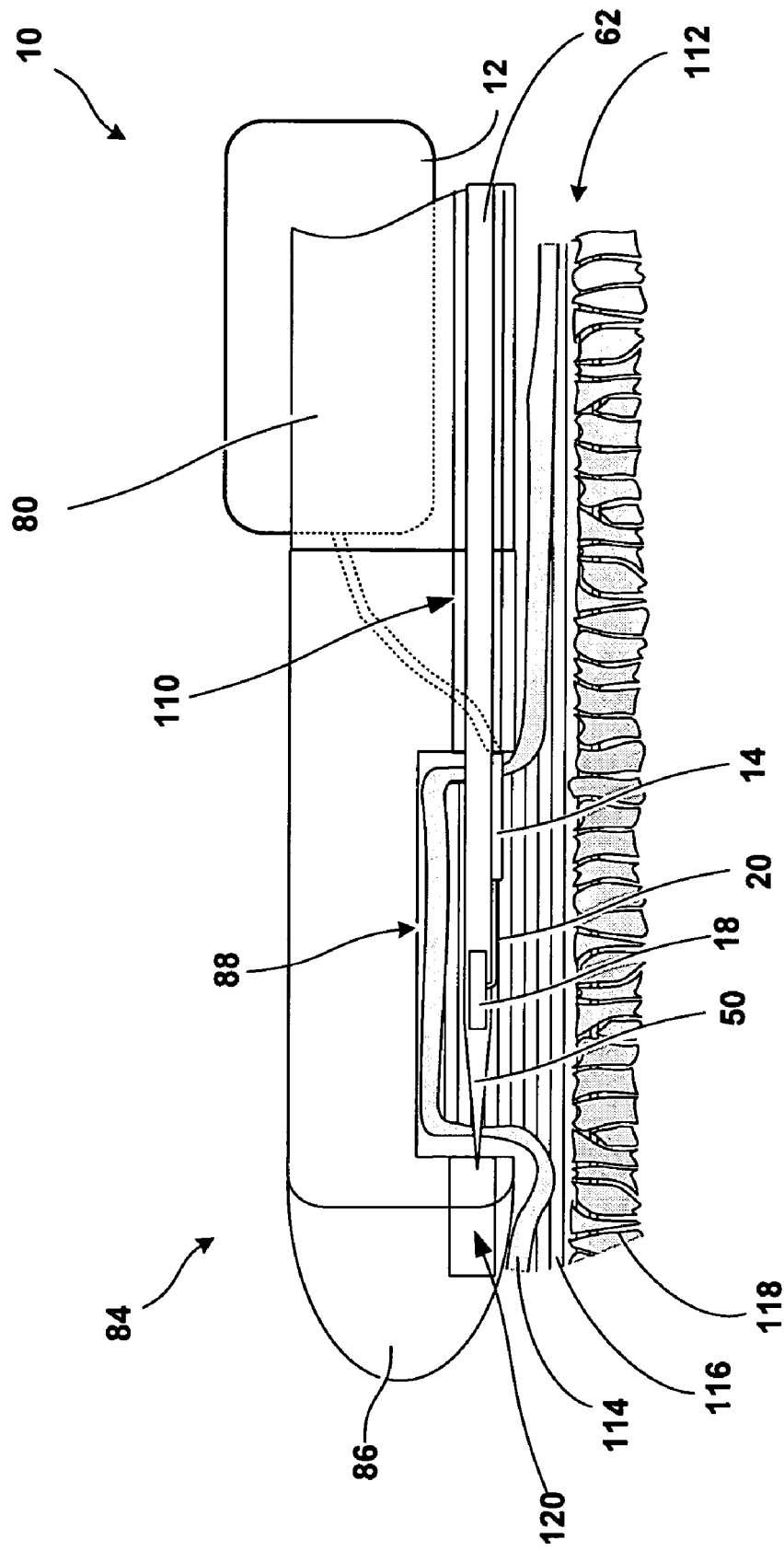

As illustrated in FIG. 6B, the user may then advance needle 50 from lumen 110 into cavity 88, and through the tissue of luminal wall 112 drawn into the cavity. By advancing through the tissue, needle 50 creates a passageway from the lumen, through the tissue, and back into the lumen. Needle 50 also places, e.g., "pulls," lead 14 of medical device 10 into the passageway.

Figure 6C:
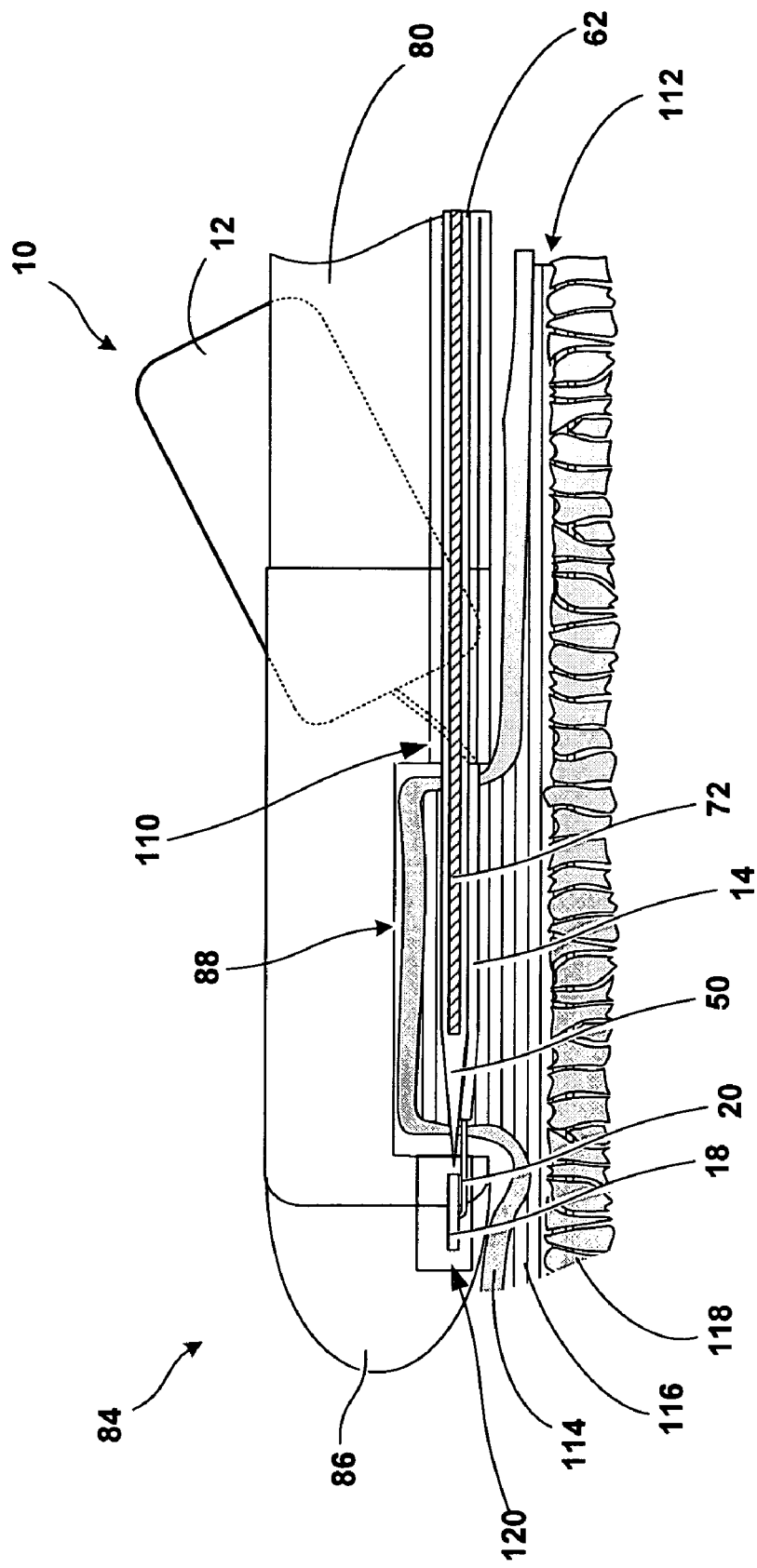

As illustrated in FIG. 6C, the user may advance elongate element 72 (shaded) of ejection tool 70 (FIG. 4C) through lumen 68 (FIG. 4B) defined by needle advancing tool 60, and through bore 52. Elongate element 72 of ejection tool 70 forces anchor member 18 out of bore 52 of needle 50, and into a receiving chamber 120 that communicates with cavity 88 and is defined by the distal portion 84 of delivery device 78. By forcing the anchor member out of the bore, ejection tool 70 places the anchor member through the tissue drawn into cavity 88 and on the distal side of the passageway formed by the needle. By forcing the anchor member 18 out of the bore, ejection tool 70 also may also pull lead 14 further into the passageway.

In some embodiments, cavity 88 may open into the lumen when engaged with luminal wall 112, e.g., distal end 86 of delivery device 78 may define an opening. In such embodiments, ejection tool 70 may force anchor member 18 out of bore 52 and into the lumen, rather than into receiving chamber 120.

Figure 6D:
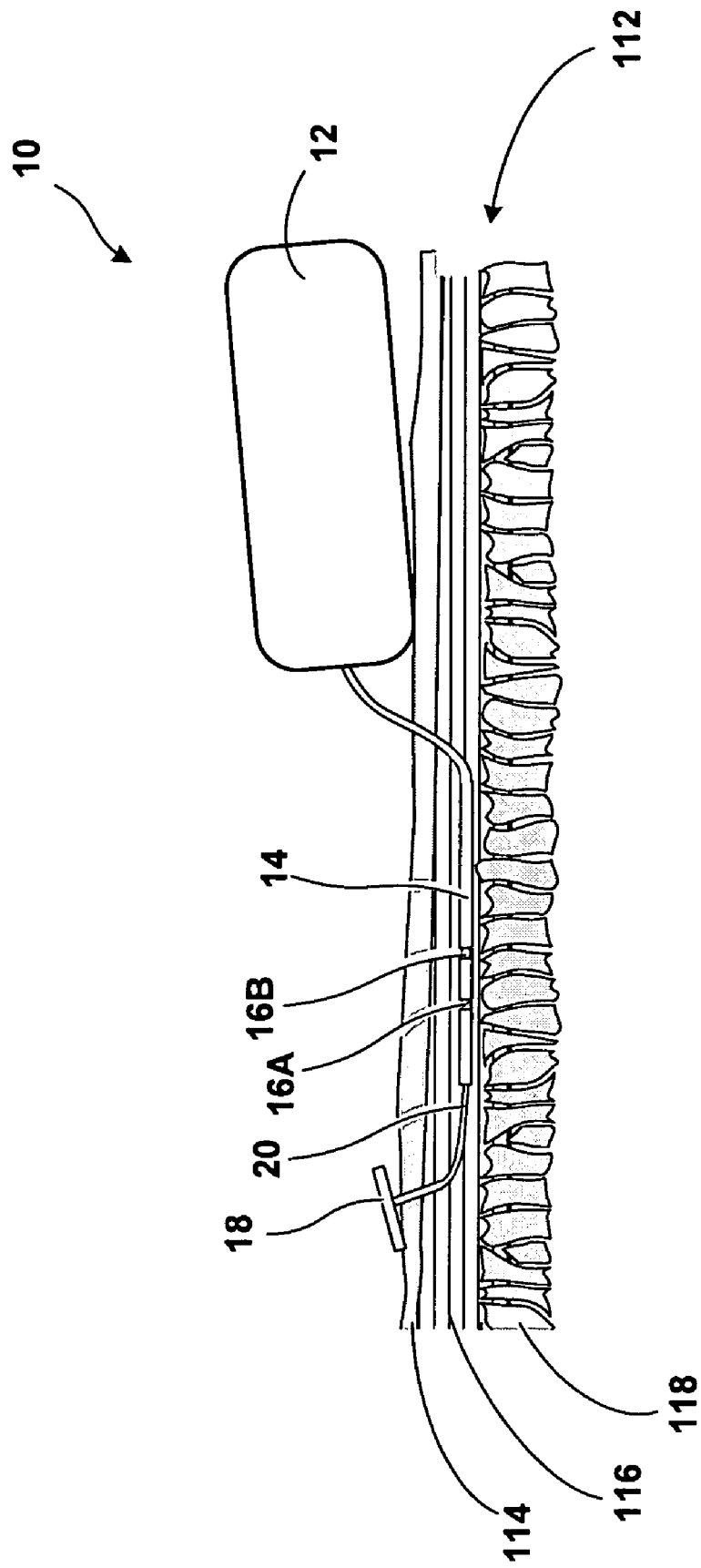

FIG. 6D illustrates medical device 10 implanted within the lumen. As illustrated in FIG. 6D, medical device 10 is attached to luminal wall 112 by lead 14. Anchor member 18 located on a first side of the passageway created by needle 50 and device housing 12 located on a second side of the passageway retain lead 14 within luminal wall 112. Electrodes 16 are located within luminal wall 112, where they may be used by the electronic circuitry within device housing 12 for stimulation and/or sensing.

In the illustrated example, lead 14 is located within submucosal layer 116 of luminal wall 112. Lead may also be located within mucosal layer 114 or muscular layer 118 of luminal wall 112. Over time, mucosal tissue may slough off, releasing medical device 10. When medical device 10 is implanted within the gastrointestinal tract of patient 100, the patient may then pass medical device 10. A user of delivery system 76 may implant lead 14 within mucosal layer 114 if temporary implantation is desired. The user may implant lead 14 within submucosal layer 116 or muscular layer 118 if a longer-term implantation is desired. The depth at which lead 14 is implanted, i.e., the depth of the passageway created by advancing needle 50 through tissue of luminal wall 112, may be selected through selection of the depth of cavity 88 defined by distal portion 84 of delivery device 78.

Medical device 10 may also be explanted by removing, e.g., cutting, anchor member 18 from the remainder of medical device 10. An endoscopic tool may grasp device housing 12, and the housing and lead 14 may be removed, or the housing and lead may be allowed to be passed by patient 100. Further, anchor member 18 and/or connecting member 20 may be formed of a degradable material that degrades or absorbs over time to release medical device 10 from luminal wall 112. Examples of suitable degradable materials for fabrication of anchor member 18 and/or connecting member 20 include bioabsorbable or dissolvable materials such as polylactic acid (PLA) or copolymers of PLA and glycolic acid, polymers of p-dioxanone and 1,4-dioxepan-2-one, or absorbable polyesters of hydroxycarboxylic acids, such as polylactide, polyglycolide, and copolymers of lactide and glycolide.

Although the elongate shape of anchor member 18 illustrated in FIG. 6D may prevent the anchor member from traveling back through the passageway through luminal wall 112 created by needle 50, anchor member 18 and/or connecting member 20 may be formed to include a hydrogel material in some embodiments to further decrease the likelihood that the anchor member will be pulled back through the passageway. The hydrogel material absorbs water and expands, e.g., after anchor member has been forced out of bore 52 of needle 50, to increase the size of the anchor member or connecting member. Suitable hydrogel materials that may be included as at least part of anchor member 18 and connecting member 20 are described in U.S. Pat. No. 6,401,718 to Johnson et al., assigned to Medtronic Endonetics, Inc., and entitled "Submucosal esophageal bulking device," the entire content of which is incorporated herein by reference.

Figure 7:
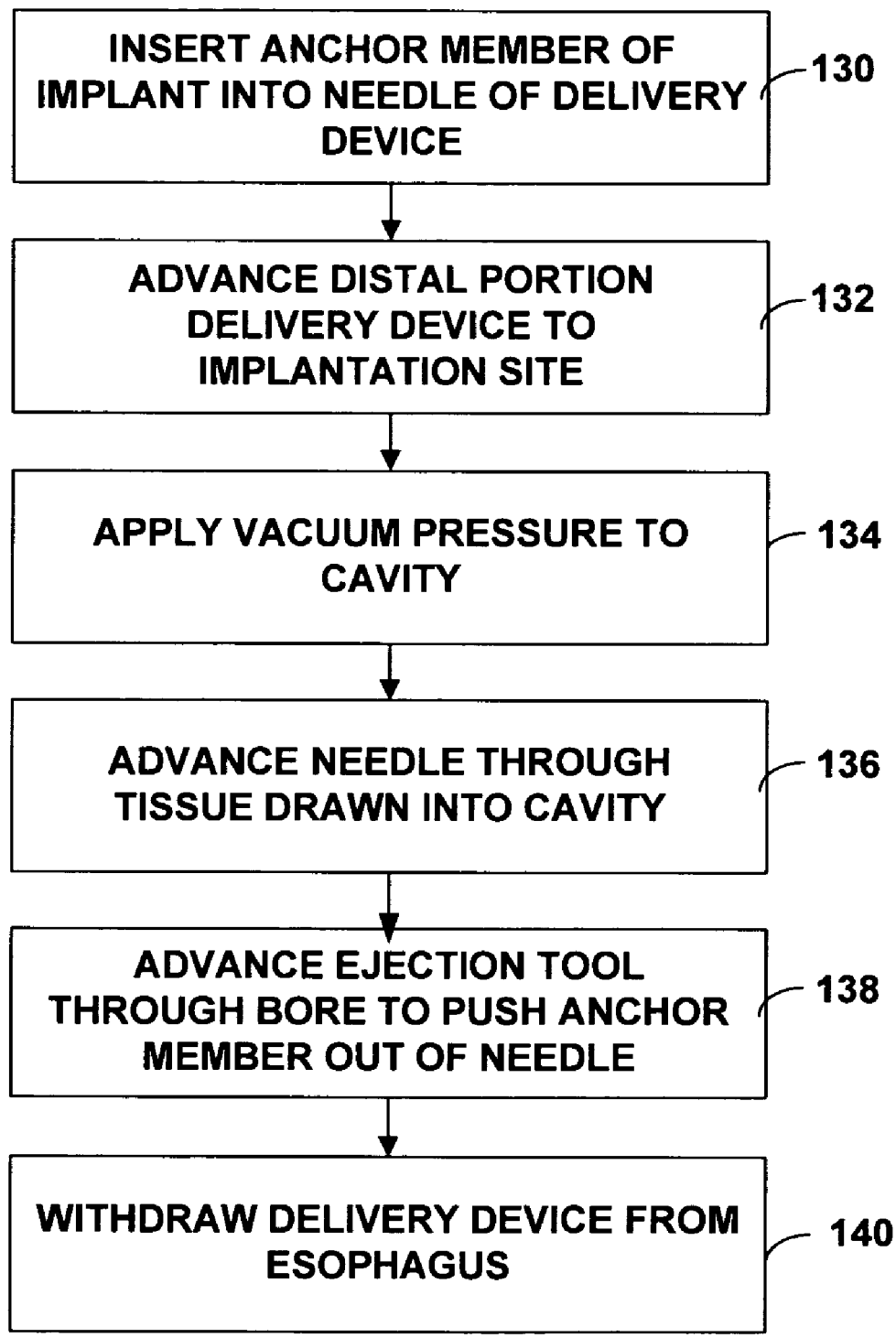
FIG. 7 is a flow diagram illustrating an example method for implanting a medical device within a lumen of a patient.

FIG. 7 is a flow diagram illustrating an example method for implanting medical device 10 within a lumen of patient 100, such as esophagus 104 or stomach 106 of the patient's gastrointestinal tract. According to the example, method, a user inserts anchor member 18 into bore 52 of needle 50, which has been advanced to distal portion 84 of delivery device 78 (130). The user may then advance distal portion 84 of delivery device 78 and medical device 10, which is attached to needle 50 by anchor member 18, to an implantation location (132).

When the distal portion 84 reaches the implantation location, the user may apply vacuum pressure to cavity 88 defined by the distal portion via vacuum ports 90 to draw tissue of luminal wall 112 at the implantation location into the cavity (134). The user advances needle 50 into the cavity and through the tissue to create a passageway from the lumen, through the tissue, and back into the lumen (136). The user advances ejection tool 70 through bore 52 to force anchor member 18 out of needle 50 at the distal side of the passageway (138). Through advancing the needle and ejecting the anchor member, lead 14 of medical device 10 is placed in the passageway with anchor member 18 located at a first side of the passageway and device housing 12 located at a second side of the passageway. Anchor member 18 and device housing 12 retain lead 14 within luminal wall 112, attaching medical device 10 to the luminal wall at the implantation location within the lumen. Delivery device 78 may be withdrawn from the lumen (140).

The preceding specific embodiments are illustrative of the practice of the invention. It is to be understood, therefore, that other expedients known to those skilled in the art or disclosed herein may be employed without departing from the invention or the scope of the claims. For example, the present invention further includes within its scope methods of making and using systems as described herein.

Further, although described herein as including electrodes located on a lead, medical devices according to the invention may additionally or alternatively include any type of sensor or therapy delivery mechanism. For example, medical devices according to the invention may additionally or alternatively include bonded piezoelectric elements, accelerometers, pressure sensors, or chemical sensors. Such sensors, or the electrodes, may not be located within a luminal wall when the medical device is implanted, and may not be carried by a lead. For example, such sensors or electrodes may be formed integrally with the housing of the medical device or the anchor member.

Further, although described herein in the context of embodiments in which a tether member that couples a medical device housing to an anchor member is a lead 14, the invention is not so limited. As discussed above, electrodes and sensors may be located in locations other than within the luminal wall tissue or on a lead. In such embodiments, a tether member need not be a lead, e.g., include conductors to couple electrodes or sensors to the electronics within the medical device housing, and may be formed of any of a variety of biocompatible materials, such as polyethylene, polyvinylchloride, or silicone.

Additionally, medical devices according to the invention may include implantable pumps. In such embodiments, the tether member may comprise a catheter through which the medical device delivers a biological, pharmaceutical, or other agent.

Further, although a delivery system has been described herein as including elongate needle advancing and ejection tools that are manipulated by a user at a handle of a delivery device, the invention is not so limited. For example, in some embodiments, a delivery device may include a needle and ejection tool coupled to one or more biased spring mechanisms, which are in turn coupled to cables or the like that connect the spring mechanisms to one or more triggers located at a handle of the delivery device. In such embodiments, a user may pull the triggers to the release the spring mechanisms, thereby advancing the needle through tissue of a luminal wall and ejecting an anchor member from a bore of the needle to attach a medical device to the luminal wall. Further, in other embodiments, the needle and/or ejection tool may be advanced by a compressed fluid, such as air, water or saline. Additionally, in some embodiments, the ejection tool that is advanceable through the needle to eject the anchor member from the bore may be a compressed fluid, such as air water or saline.

Several embodiments of the present invention are described above. It is to be understood that various modifications may be made to those embodiments of the present invention without departing from the scope of the claims. These and other embodiments are intended to fall within the scope of the appended claims.

The invention claimed is:

1. A system for implantation of a medical device within a lumen of a patient, the system comprising:
  the medical device, wherein the medical device comprises:
    a device housing sized for introduction into the lumen,
    electrical circuitry mounted within the device housing,
    a tether member that includes a proximal end that is coupled to the device housing, and
    an anchor member located at a distal portion of the tether member;
  an elongated delivery device with a distal portion that defines a cavity;
  a vacuum port to draw tissue of a wall of the lumen into the cavity;
  a needle that defines a bore, wherein the bore receives the anchor member of the medical device, and wherein the needle is advanceable into the cavity and through the tissue disposed in the cavity while the anchor member is received by the bore to form a passageway from the lumen, through the tissue, and back into the lumen and to place the tether member within the passageway; and
  an ejection tool that is advanceable through the bore of the needle to eject the anchor member from the bore when the needle has been advanced though the tissue such that the anchor member is in the lumen on a first side of the passageway through the tissue and the device housing is in the lumen on a second side of the passageway through the tissue.

2. The system of claim 1, wherein the tether member comprises a lead that includes at least one electrode located between the proximal end and the anchor member and coupled to the electrical circuitry within the device housing.

3. The system of claim 1, wherein the anchor member is elongate.

4. The system of claim 1, wherein the anchor member is substantially cylindrical.

5. The system of claim 1, wherein the anchor member has a width that substantially corresponds to the bore of the needle.

6. The system of claim 1, wherein the width of the anchor member is less than approximately 0.1 inches.

7. The system of claim 1, wherein the width of the anchor member is within a range from approximately 0.04 inches to approximately 0.06 inches.

8. The system of claim 1, wherein the width of anchor member is approximately 0.05 inches.

9. The system of claim 1, wherein the anchor member is sized to frictionally engage the needle when received by the bore of the needle.

10. The system of claim 1, wherein a longitudinal axis of the anchor member is substantially perpendicular to a longitudinal axis of the tether member.

11. The system of claim 1, wherein the needle further defines a slot that extends from a distal end of the needle.

12. The system of claim 11, wherein the slot extends axially from the distal end of the needle.

13. The system of claim 11, wherein a width of the slot is less than a width of the bore.

14. The system of claim 11, wherein the medical device further comprises a connecting member that connects the anchor member to the tether member, has a width that is less than a width of the anchor member and the tether member, and passes through the slot when the anchor member is received by the bore.

15. The system of claim 14, wherein the width of the connecting member substantially corresponds to a width of the slot.

16. The system of claim 14, wherein the connecting member is sized to frictionally engage the needle when passed through the slot.

17. The system of claim 11, wherein a width of the distal portion of the tether member is less than a width of the anchor member, and the distal portion of the tether member passes through the slot when the anchor member is received by the bore.

18. The system of claim 17, wherein the width of the distal portion of the tether member substantially corresponds to a width of the slot.

19. The system of claim 17, wherein the distal portion of the tether member is sized to frictionally engage the needle when passed through the slot.

20. The system of claim 1, wherein the distal portion of the elongated delivery device further comprises a receiving chamber in fluid communication with the cavity, the needle is advanceable through the tissue and into the receiving chamber, and the ejection tool ejects the anchor member into the receiving chamber.

21. The system of claim 1, wherein the elongated delivery device comprises an endoscopic delivery device.

22. A method for implanting a medical device within a lumen of a patient, the method comprising:
  inserting an anchor member of the medical device into a bore of a needle;
  advancing the needle through tissue of the lumen with the anchor member inserted in the bore to create a passageway from the lumen, through the tissue, and back into the lumen, and to place a tether member of the medical device coupled to the anchor member within the passageway; and
  ejecting the anchor member from the bore to place the anchor member in the lumen on a first side of the passageway while a device housing of the medical device coupled to the tether member is located in the lumen on a second side of the passageway, wherein the anchor member and the device housing keep the tether member within the passageway.

23. The method of claim 22, further comprising drawing tissue of the lumen into a chamber of an elongated delivery device, wherein advancing the needle into tissue comprises advancing the needle though the tissue drawn into the chamber.

24. The method of claim 22, wherein the tether member comprises a lead that includes at least one electrode located between the proximal end and the anchor member and coupled to the electrical circuitry within the device housing, and the method comprises placing the electrode within the passageway through the tissue.

25. A system for implantation of a medical device within a lumen of a patient, the system comprising:
  the medical device, wherein the medical device comprises:
    a device housing sized for introduction into the lumen,
    electrical circuitry mounted within the device housing,
    a tether member that includes a proximal end that is coupled to the device housing, and an anchor member located at a distal portion of the tether member;

an elongated delivery device with a distal portion that defines a cavity;

a vacuum port to draw tissue of a wall of the lumen into the cavity;

a needle that defines a bore, wherein the bore receives the anchor member of the medical device, and the needle is advanceable into the cavity and through the tissue disposed in the cavity while the anchor member is received by the bore to form a passageway from the lumen, through the tissue, and back into the lumen and to place the tether member within the passageway; and an ejection tool that is advanceable through the bore of the needle to eject the anchor member from the bore when the needle has been advanced though the tissue such that the anchor member is in the lumen on a first side of the passageway through the tissue and the device housing is in the lumen on a second side of the passageway through tissue, wherein the tether member comprises a lead that includes at least one electrode located between the proximal end and the anchor member and coupled to the electrical circuitry within the device housing.

* * * * *